US005447644A

United States Patent [19]

Guénin et al.

[11] Patent Number: 5,447,644

[45] Date of Patent: Sep. 5, 1995

[54] METHOD OF CONTROLLING VISCOSITY OF FABRIC SOFTENERS

[75] Inventors: Eric P. Guénin, Piscataway; Leslie C. Smith, Plainsboro, both of N.J.

[73] Assignee: International Flavors & Fragrances Inc., New York, N.Y.

[21] Appl. No.: 242,341

[22] Filed: May 12, 1994

[51] Int. Cl.[6] .................... A61K 7/46; D06M 13/00

[52] U.S. Cl. .................... 252/8.6; 512/2

[58] Field of Search .................... 512/2; 252/8.6

[56] References Cited

U.S. PATENT DOCUMENTS

| | | | |
|---|---|---|---|
| 4,446,032 | 5/1984 | Munteanue et al. | 252/8.6 |
| 5,190,915 | 3/1993 | Behan et al. | 512/2 |
| 5,246,918 | 9/1993 | Behan et al. | 512/2 |
| 5,252,555 | 10/1993 | Dartnell | 512/4 |

*Primary Examiner*—Mark L. Bell
*Assistant Examiner*—C. M. Bonner
*Attorney, Agent, or Firm*—Arthur L. Liberman

[57] ABSTRACT

A method is disclosed for controlling the viscosity of fabric softener compositions to thereby improve shelf life by first forming a microemulsion of a perfume and a surfactant by mixing a perfume and a surfactant at a temperature where each component is in the liquid state. Sufficient shearing forces are used to uniformly disperse the perfume in the surfactant to form a stable microemulsion of said perfume in said surfactant. The microemulsion is then mixed with a fabric softener base formulation.

8 Claims, 9 Drawing Sheets

METHOD OF CONTROLLING VISCOSITY OF FABRIC SOFTENERS

BACKGROUND OF THE INVENTION

The present invention relates to a method of controlling the viscosity of fabric softening compositions and, more particularly, to a method for avoiding gelation or gel formation of fabric softener compositions.

Fabric softening agents are used in order to improve the feel and texture of fabrics and to improve the comfortability of fabrics in actual wear. More particularly, fabric softeners have the effect of reducing the static charge on man-made fabrics and give a softer feel to cotton articles. They usually contain from 4–8% cationic detergent material and are pourable, easily-dispersed liquids. Sodium chloride or acetate are used to lower the viscosity while addition of methylcellulose or long chain alcohol increases viscosity. The structures responsible for viscosity are the multiwalled vesicles (similar to liposomes) formed by the surfactant. If small amounts of ionic or non-ionic materials are added to the system slow osmotic swelling or shrinkage of the vesicles can occur leading to marked changes in viscosity on storage. As the concentration of the surfactant increases in the fabric softener, the concentration and size of the vesicles increases. Therefore rheological behavior becomes a real issue for the product.

Typically, fabric softening agents are applied from an aqueous liquid which is made up by adding a relatively small amount of a fabric softening composition to a large amount of water, for example during the rinse cycle in an automatic washing machine. The fabric softening composition is usually an aqueous liquid product containing between about 8% and 25% of a cationic fabric softening agent which is a quaternary ammonium salt. Such compositions are normally prepared by dispersing in water a cationic material, for example quaternary ammonium compounds which in addition to long chain alkyl groups may also contain ester or amide groups. It is also advantageous to use mixtures of different fabric softening components which are typically added to the last wash cycle rinse both in the form of aqueous dispersions.

It is widely known that fragrances can be introduced into liquid fabric softener compositions in order to cause the treated fabrics to have aromas with good initial strength. Efforts have also been made to develop systems in which aromas are controllably released during the normal conditions of use of the fabrics treated with solutions created from the liquid softening compositions of matter at a predictable sufficiently high level over an extended period time.

It is recognized in the prior art that perfume containing particles of a defined melting point and size can be incorporated into compositions containing fabric softening components. Typical of such prior art is Canadian Patent 1,111,616, German OLS 2631129, German OLS 2702162, U.S. Pat. Nos. 4,234,627 and 4,464,271.

Since the early '80's, fabric softeners have been on the market in a concentrated form of one type or another. Normal concentrations for fabric softeners typically range from 3 to 7% active ingredients. The concentrates came into the market at 3 to 6 times the normal surfactant concentration. Thus the concentrated forms of fabric softeners can contain 10 to 50% surface active agent.

However it has been found that when the amount of fragrance is increased beyond just one, two or three percent, there is a tendency for the fabric softener base formulation to gel. Undesirable gelation of the fabric softener reduces the shelf life of the product and may cause an adverse consumer reaction when the person using the fabric softener opens the container and finds that the fabric softener has formed a gel like, highly viscous mass instead of being free flowing.

This tendency of gel formation has prevented the utilization of larger amounts of fragrances or the use of large amounts of fragrances with a relatively weak aroma creating power.

Various efforts have been made to influence the viscosity of fabric softeners to overcome certain problems and to improve properties. For example, low viscosity concentrated products as shown in U.S. Pat. No. 3,681,241 contain ionizable salts, fatty acids, fatty alcohols, fatty esters and paraffinic hydrocarbons. See also European patent 13780.

It has also been proposed in European patent specification 56695 to control the viscosity of concentrated products by the use of small amounts of alkoxylated amines.

Still further developments are shown in U.S. Pat. No. 4,497,716 where there is disclosed a concentrated liquid fabric softening composition which contains a water soluble cationic fabric softening agent, a nonionic viscosity control agent and an electrolyte. The viscosity control agent is an alkylene oxide adduct of a fatty compound selected from fatty amines, fatty alcohols, fatty acids and fatty esters.

It is therefore an object of the present invention to provide a way to avoid gelation in fragrance containing fabric softening agents and also to provide a way to permit the introduction of an increased amount of fragrance into a fabric softening composition.

SUMMARY OF THE INVENTION

It is an object of the present invention to provide a method for controlling the viscosity of a fabric softener to thereby enable the production of fabric softeners which have a reduced tendency to gel.

It is a further object of the present invention to provide for the control of fabric softener viscosity by increasing the amount of fragrance in the formulation and to thereby influence the amount of fragrance that can be added to the fabric softening formulations.

In achieving the above and other objects, one feature of the present invention resides in a method for controlling viscosity of a fabric softener by first preparing a microemulsion of a perfume or fragrance chemical and a surface active agent. Thereafter the microemulsion is added to a fabric softener base formulation to produce the fabric softener consumer product.

According to one embodiment of the invention, the method for controlling the viscosity of fabric softener compositions to improve shelf life is carried out by mixing a perfume and a surfactant at a temperature where each component is in the liquid state, and under conditions of sufficient shearing forces to uniformly disperse the perfume or aroma chemical component in the surfactant to form a stable microemulsion of the perfume in the surfactant. Then the microemulsion and a fabric softener base formulation are mixed together in sufficient amounts to form a fabric softener composition which avoids gelation. The surfactant used in the above method has a high HLB number; i.e 13 or greater. Preferably the surfactant is used in the proportion of 3 parts per part of perfume and the mixing of the perfume and surfactant takes place under conditions which prevent air entrainment.

Control of viscosity is obtained in the present invention by using microemulsion systems composed of a high HLB surfactant which isolate the fragrance from the fabric softener droplets or vesicles. In a further embodiment of the present invention, the composition of the microemulsion system can be modified to also improve the substantivity profile. In carrying out this second embodiment of the invention, there was included in the formulation some agents which would provide substantivity enhancement. The addition of a low HLB surfactants in concentration 10 to 25% of the total surfactant concentration (0.8 to 2% of total fabric softener composition) improved the final substantivity of the fragrance on wet clothes. This may be due to their adherence to clothes in the form of crystal structures and the affinity of the fragrance for this type of systems.

BRIEF DESCRIPTION OF THE DRAWINGS

The present invention will be further understood with reference to the drawings, wherein.

DETAILED DESCRIPTION OF INVENTION

Figure 1:
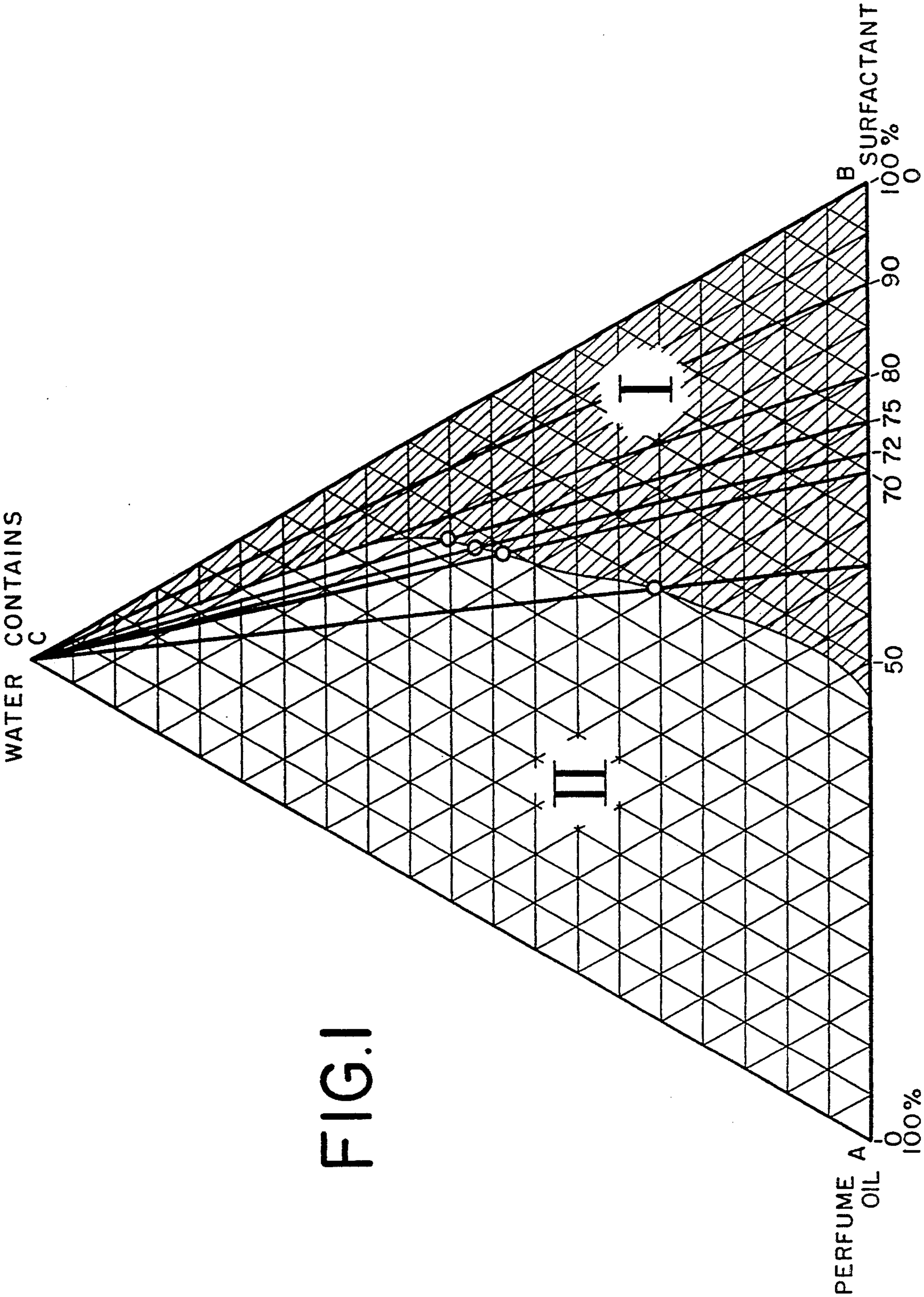
FIG. 1 is a phase diagram showing the region of microemulsion and emulsion phase using one type of surface active agent in accordance with the invention.

In carrying out the present invention, there is provided a method for avoiding the gelation of fabric softeners by mixing a perfume component and a special surface active component to form a stabilized microemulsion. Subsequently, this stabilized emulsion is compounded with a fabric softener base formulation in accordance with conventional technology.

The invention provides a process for incorporating a perfume into a fabric softener base of a wide variety, whereby the perfume is first combined with one or more non-ionic emulsifiers and an aqueous phase to form a structured microemulsion containing liquid crystal structures, which surround and protect the dispersed perfume. The result is a stable emulsion. Thereafter this structured and stable emulsion is dispersed into a fabric softener base, to produce a fabric softener product with improved perfume performance. Hence, the invention provides fabric softener products obtainable by this process and perfume containing structured emulsions used in this process.

According to the invention the structured microemulsion is produced by first forming a non-aqueous phase comprising the perfume, a non-ionic emulsifier or an emulsifier mixture based on non-ionic emulsifiers, and optionally other adjuncts, which are mixed at a temperature at which the non-aqueous phase forms a homogeneous liquid. Then an aqueous phase is formed consisting of water or an aqueous mixture containing water-soluble and/or water-dispersible materials and the two phases are mixed under shear conditions.

The structured emulsions herein contain 1–10% by weight of perfume in a structured system comprised basically of one or more non-ionic emulsifiers totalling 1–30% by weight and 20–89% by weight of water or an aqueous mixture containing water-soluble and/or water-dispersible materials, hereinafter jointly referred to as "aqueous phase". Such water-soluble or water-dispersible materials may form up to 30% by weight of the aqueous phase and will hereinafter be referred to as hydrophilic adjuncts. The structured emulsion system is characterized by possessing liquid crystalline layers which surround the droplets of perfume.

Optionally, other hydrophobic adjuncts may be mixed with the perfume and thus be present in the non-aqueous phase at a total level of 0–30% by weight of the non-aqueous phase. For the purpose of this invention it is necessary that the total perfume or perfume/hydrophobic adjunct mixture is hydrophobic in nature as otherwise the emulsion will not form correctly. With the expression "hydrophobic" as used herein is meant a material which will be soluble in one or more organic solvents such as ethanol, acetone or hydrocarbon solvents and will not exhibit an appreciable degree of solubility in water.

In this connection there may be mentioned well known low HLB surfactants such as those known as SPAN® by ICI which are mixtures of partial esters of sorbitol and fatty acids. These are discussed hereinafter in connection with a second embodiment of the invention. Examples include, sorbitan laurate, palmitate, stearate, and the like. An amount of up to 1 per 100 parts of non-ionic surfactant is typically used.

A low quantity (e.g. up to 1%) of polyethylene glycol can also be present in this admixture. The Carbowax® materials are known for this purpose.

The non-ionic emulsifiers will preferably be present in the structured emulsion at 3–30% by weight, more preferably 10–20%; the perfume (or perfume/hydrophobic adjuncts mixture) preferably at 1–10% by weight, more preferably 3–6%, and the aqueous phase preferably at 60–95% by weight, more preferably at least 60%, particularly 60–80%. It is particularly suitable that the weight ratio of total emulsifier to perfume lies within the range 3:1 to 6:1, preferably 3:1, and the weight ratio of non-aqueous phase to aqueous phase lies within the range 1:2 to 4:3, preferably within 1:2 to 1:100. The hydrophobic and hydrophilic adjuncts may together comprise up to 30% by weight of the structured emulsion but preferably comprise no more than 20% by weight.

By using the fragrance/surfactant microemulsion mixture of the present invention instead of adding a fragrance oil to a fabric softener base it is possible to obtain a relative decrease in the viscosity of the final fabric softener product. Thus it is possible to avoid long term irreversible thickening of the fabric softener and allow maintenance of a pourable product.

Among the fabric softening base formulations that can be used in accordance with the present invention, there are any of the well known species of substantially water insoluble mono-ammonium compounds which are the quaternary ammonium and amine salt compounds having the formula:

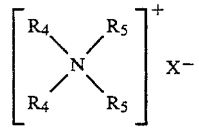

wherein each $R_4$ represents alkyl or alkenyl groups of from about 12 to about 24 carbon atoms optionally interrupted by amide, propyleneoxy groups and the like. Each $R_5$ represents hydrogen, alkyl, alkenyl or hydroxyalkyl groups containing from 1 to about 4 carbon atoms; and X is the salt counteranion, preferably selected from halide, methyl sulphate and ethyl sulphate radicals. Such materials are well known in the art.

Representative examples of these quaternary softeners include ditallow dimethyl ammonium chloride, ditallow dimethyl ammonium methosulphate; dihexadecyl dimethyl ammonium chloride; di(hydrogenated tallow alkyl)dimethyl ammonium chloride; dioctadecyl dimethyl ammonium chloride; dieicosyl dimethyl ammonium chloride; didocosyl dimethyl ammonium chloride; di(hydrogenated tallow)dimethyl ammonium methyl sulphate; dihexadecyl diethyl ammonium chloride; di(coconut alkyl)dimethyl ammonium chloride; di(coconut alkyl)dimethyl ammonium methosulphate; di(tallowyl amido)ethyl dimethyl ammonium chloride and di(tallowyl amido)ethyl methyl ammonium methosulphate. Of these, ditallow dimethyl ammonium chloride and di(hydrogenated tallow alkyl)dimethyl ammonium chloride are preferred.

Another preferred class of water-insoluble cationic materials which can be present in the fabric softener base are the alkyl imidazolinium salts believed to have the formula:

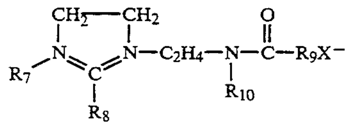

wherein $R_7$ is hydrogen or an alkyl containing from 1 to 4, preferably 1 or 2 carbon atoms, $R_8$ is an alkyl containing from 12 to 24 carbon atoms, $R_9$ is an alkyl containing from 12 to 24 carbon atoms, $R_{10}$ is hydrogen or an alkyl containing from 1 to 4 carbon atoms and X is the salt counteranion, preferably a halide, methosulphate or ethosulphate. Preferred imidazolinium salts include 3-methyl-1-(tallowyl amido)ethyl-2-tallowyl-4,4-dihydroimidazolinium methosulphate and 3-methyl-1-(palmitoyl amido)ethyl-2-octadecyl-4,5-dihydroimidazolinium chloride. Other useful imidazolinium materials are 2-heptadecyl-3-methyl-1-(2-stearylamido)-ethyl-4,5-dihydroimidazolinium chloride and 2-lauryl-3-hydroxyethyl-1-(oleylamido)ethyl-4,5-dihydro imidazolinium chloride.

Like the quats, they are usually supplied at ca. 75 wt % active matter and in this form, the hard tallow is pumpable at 40° C., soft tallow at 27° C. and the oleyl derivative at 18° C. Theses figures illustrate why the oleyl variant is very popular with manufacturers who wish to process at ambient temperatures.

In Europe, there has been increasing demand for conditioner chemicals which can be formulated at up to 25% w in liquid fabric conditioner concentrates and be diluted before use by the consumer. Moreover, such products are expected to combine a fabric softening property which is equivalent to that of the DSDMAC compounds without inherent disadvantages of having to store and process raw materials at >50° C. and having to safeguard against fabric waterproofing if the end product is over-dosed. The "ester quats" have achieved popularity in recent years in this context. Some reported structures are illustrated below and are all characterized in that the side chains contain an ester group in conjunction with a fatty group (R) which is derived from "soft" (tallow) fatty acids.

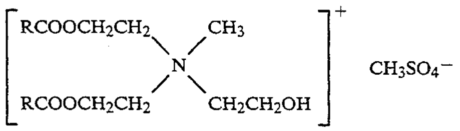

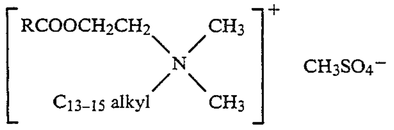

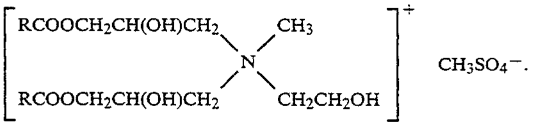

Some insights into the manufacture and thereby trace components can be obtained from the prior art patents such as EP 165 138, U.S. Pat. No. 4,370,272, GB 2,015,051, and EP 90 117. Generally speaking, the ester quats should be formulated at more acid pH values than the pH5-6 which is a feature of conventional fabric conditioners. If this is not done, there is a tendency for the side chains to hydrolyze.

The most commercially significant group of amidoamines comprise alkyl moieties (R) which may be chosen from hard or soft tallow or oleic acids. The manufacture of the products is initially similar to the procedure used for the imidazolines but the diamidoamine is not cyclized.

Commercially available fabric softeners often contain considerable quantities of solvents, in particular iso-propanol. It is desirable that the composition contains no more than about 2.5% by weight of iso-propanol or any other monohydric alcohol having 1 to 4 carbon atoms.

Additionally the composition can contain substances for maintaining stability of the product in cold storage. Examples of such substances include polyhydric alcohols such as ethylene glycol, propylene glycol, glycerol and polyethylene glycol. A suitable level for such materials is from about 0.5% to about 5%, preferably about 1 to 2% by weight.

Fabric softeners typically also include other ingredients including colorants, preservatives, anti-foaming agents, optical brighteners, opacifiers, pH buffers, further viscosity modifiers, anti-shrinkage agents, anti-wrinkle agents, fabric crisping agents, spotting agents, soil-release agents, germicides, anti-oxidants and anti-corrosion agents.

As employed herein and in appended claims the term "perfume" is used in its ordinary sense to refer to and include any essentially water insoluble fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders and stabilizers. These auxiliaries are also included within the meaning of "perfume" as used herein. Typically, perfumes are complex mixtures of a plurality of organic compounds, which may include odoriferous or fragrant essential hydrocarbons, such as terpenes, ethers and other compounds which are of acceptable stabilities in the present compositions. Such materials are either well known in the art or are readily determinable by simple testing, and so need not be listed in detail here.

The perfumes employed in the invention will preferably be of a polar nature and lipophilic, so that they form at least a significant part of the oil phase of the microemulsion. Such perfumes will be hypochlorite-stable, of course, and it has been noted that the best perfumes for this purpose are those which are in the following olfactory families: floral, including floral, green floral, woody floral and fruity floral; chypre, including floral aldehydic chypre, leather chypre and green chypre; fougere; amber, including floral woody amber, floral spicy amber, sweet amber and semifloral amber; and leather. Such perfumes should be tested for hypochlorite stability before being used in these microemulsions.

Perfume components and mixtures thereof which can be used for the preparation of such perfumes may be natural products such as essential oils, absolutes, resinoids, resins, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are geraniol, geranyl acetate, linalool, linaly acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenylcarbinyl methylphenylcarbinyl acetate, p-tert-butyl-cyclohexyl acetate, isononyl acetate, vetiveryl acetate, vetiverol, alpha-n-amylcinammic aldehyde, alpha-hexyl-cinammic aldehyde, 2-methyl-3-(p-tert-.butylphenyl)-propanal, 2-methyl3-(p-isopropylphenyl)propanal, 3-(p-tert.butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3pentyltetrahydropyran, methyl dihydrojasmonate, 2-n-heptylcyclopentanone, 3-methyl-2-pentylcyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetal, 3-isocamphylcyclohexanol, cedryl methyl ether, isolongifolanone, aubepine nitrile, aubepine, heliotropine, coumarin, eugenol, vanillin, diphenyl oxide, hydroxycitronellal ionones, methyl ionones, isomethyl ionomes, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Suitable solvents, diluents or carriers for perfumes as mentioned above are for examples; ethanol, isopropanol, diethylene, glycol monoethyl ether, dipropylene glycol, diethyl phthalate, triethyl citrate, etc.

The fabric softening compositions provided are in the form of aqueous dispersions which contain about 3 to 35% of fabric softener and from about 0.5 to 25%, preferably from about 1 to about 15% of the fragrance/surfactant complex. The fragrance component is preferably dispersed in the surfactant emulsion to form a stable micro-emulsion system.

The lower limits are amounts needed to contribute to effective fabric softening performance when added to laundry rinse baths in the manner which is customary in home laundry practice. The higher limits are suitable for concentrated products which provide the consumer with more economical usage because of the reduction in packaging and distribution costs.

The pH of such compositions in a 10% solution is typically less than about 5 and more typically from about 2 to 5.

In preparing the fragrance/surfactant emulsion formulation of the present invention, the following procedures are used. A perfume is selected and a surfactant is selected for mixture at a temperature above the melting point of the surfactant. The mixture is then cooled down to room temperature and subjected to high shear mixing using a high shear mixing device such as a blade mixer with a zero angle. These blades are chosen because they allow minimum amount of air to be introduced into the system; mixing under vacuum would be an even better process.

The fabric softener which does not contain a fragrance and is in the form of a typical base formulation is then mixed with the fragrance/surfactant component. The fragrance/surfactant preparation is added slowing up to the desired quantity and the preparation is mixed for an additional period of time in order to uniformly distribute the fragrance/surfactant preparation into the fabric softener base composition.

After incorporation into fabric softeners, the perfume will stay within the micelle or emulsion droplet formed by the high HLB surfactant instead of migrating into the bilayer of the cationic surfactant vesicle of the fabric softener.

A high shear mixer is used such as manufactured by Silverson. The stator/rotor design enables emulsions to be prepared in the range of 0.5 to 5 microns. With this high shear action, the material is rapidly dispersed, constantly exposing increasing areas of the solid to the surrounding liquid. The action of the mixer can be described as taking place in four stages as follows: in stage 1 the high speed rotation of the rotor blades within the precision machined mixing workhead exerts a powerful suction, drawing liquid and solid materials upwards from the bottom of the vessel and into the center of the workhead; in stage 2, centrifugal force then drives materials towards the periphery of the workhead where they are subjected to a milling action in the precision machined clearance between the ends of the rotor blades and the inner wall of the stator; in stage 3, an intense hydraulic shear takes place as the materials are forced, at high velocity out through the perforations in the stator and circulated into the main body of the mix; and in stage 4, the materials are expelled from the head and are projected radially at high speed towards the sides of the mixing vessel. At the same time fresh material is continually drawn into the workhead maintaining the mixing cycle. The effect of the horizontal (radial) expulsion and suction into the head is to set up a circulatory pattern of mixing which is all below the surface.

As a result there is no unnecessary turbulence at the surface. So long as the machine is correctly chosen for size and power, the entire contents of the vessel will pass hundreds of times through the workhead during the mixing operation to give uniform progressive processing and homogenization. A further benefit derived from the controlled mixing pattern is that aeration is minimized.

It is preferred that the type of surfactant used in this process be of a large hydrophilic-lipophilic balance (HLB) to produce a more stable micelle, typically an HLB of at least 13. Generally, the preferred surfactants are ethers or esters of fatty acids and polyoxyethylene glycols, also called ethoxylated nonionic emulsifiers. Also, ethers and esters of polypropylene glycol and fatty acids are useful. A commercially available material called Cremophor RH 40® (a product of BASF) is a nonionic solubilizing and emulsifying agent produced by reacting one mole of hydrogenated castor oil with 40 to 50 moles of ethylene oxide.

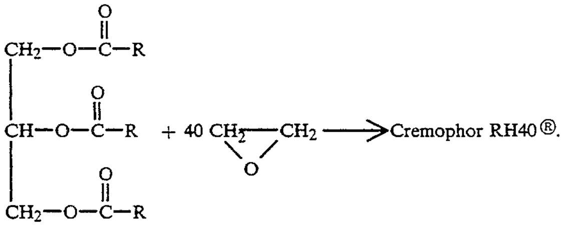

The resulting complex has a hydrophilic portion of polyethylene glycols and ethoxylated glycerine:

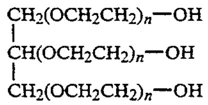

and $H(OCH_2CH_2)_n$—OH.

The hydrophobic portion is formed of ethyoxylated glycerine esters and PEG esters.

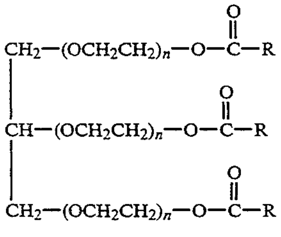

and

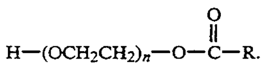

The castor oil used as a starting material is of DAB 9 quality. This material is also available with a 10% water content. In general it is used to solubilize essential oils and perfumery synthetics in aqueous alcohol and aqueous media.

Of particular interest are the polyoxyethylene sorbitan esters sold under the trademark TWEEN® such as polyoxyethylene 220 sorbitan monolaurate, monooleate and the like. Also noted are the polyoxyethylene fatty esters derived from lauryl, cetyl, stearyl and oleyl alcohols such as BRIJ® esters (polyoxyethylene 20 stearyl ether BRIJ 78®). Another suitable type are the sorbitan fatty acid esters known or ARLACEL® such as sorbitan monostearate and the like as well as the glycerol stearate, oleates etc. Another group of suitable surfactants are those marketed by ICI under the name MYRJ® which are polyoxyethylene derviatives of stearic acid. These are hydrophilic and soluble or dispersible in water. Examples include polyoxyethylene 8 sterate, polyoxyethylene 40 sterate, polyoxyethylene 50 sterate and polyoxyethylene 100 sterate.

Figure 2:
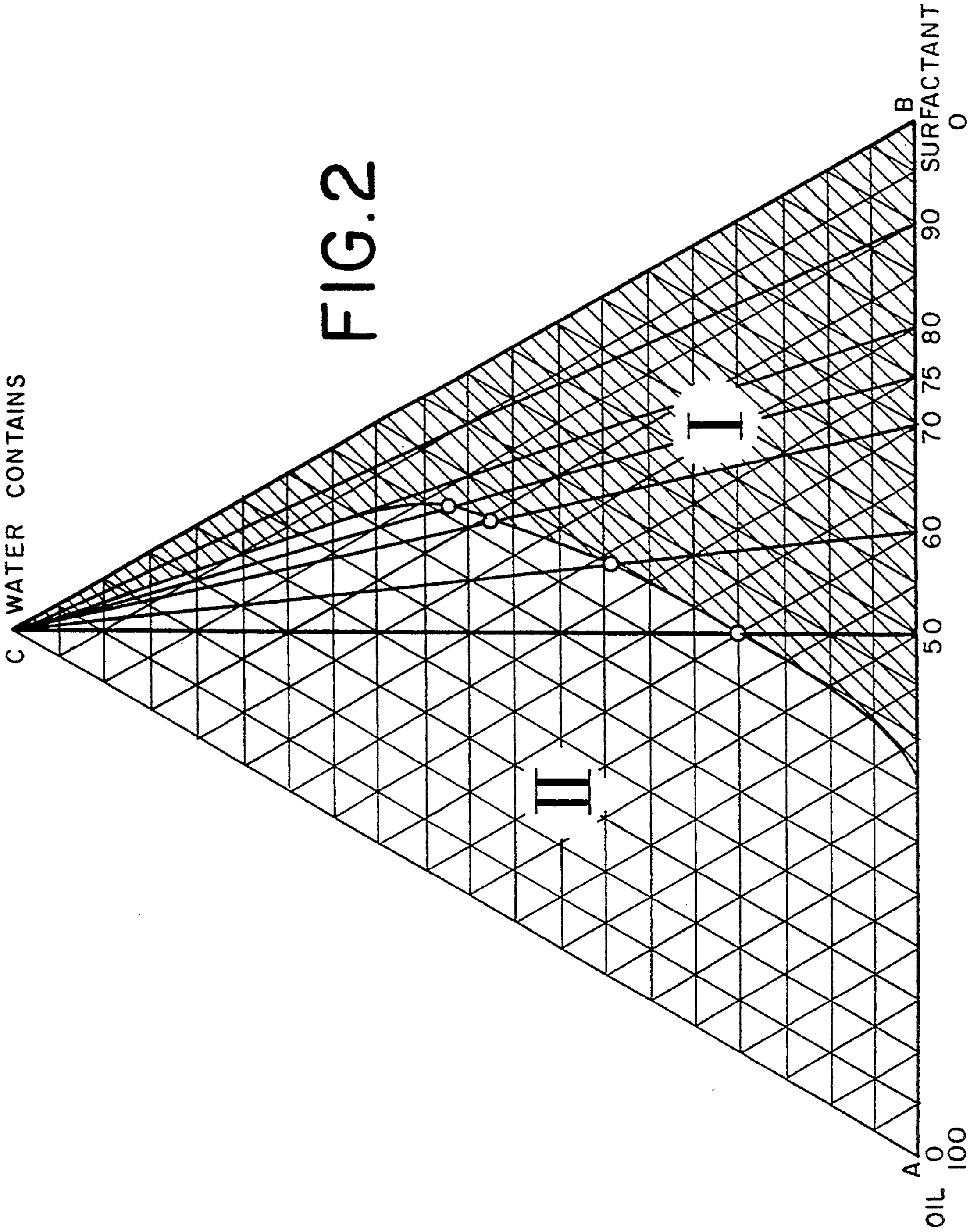
FIG. 2 is a phase diagram showing the region of microemulsion and emulsion phase using another type of surface active agent in accordance with the invention.

The structured emulsions described herein can be formed under a variety of conditions, according to the particular emulsifiers chosen and the perfume to be emulsified. In general, the method of manufacture consists of separately forming the non-aqueous phase and the aqueous phase and then mixing the two phases under shearing conditions to form the final emulsion and continuing to mix while bringing the mixture to ambient temperature. The mixing process is rapid in most cases with high shear, but for more viscous products (i.e. high emulsifier levels or viscous perfumes) it may be necessary to mix slowly or over an extended period to produce a homogeneous composition. The non-aqueous phase consists of the perfume (or perfume/hydrophobic . adjuncts mixture), emulsifier (mixture) and optional structuring aid, and is mixed at a temperature at which it forms a homogeneous liquid, wherein "homogeneous" is defined as the absence of discrete solid particles or droplets of liquid in the non-aqueous phase. The aqueous phase, optionally containing up to 30% by weight of hydrophilic adjuncts, is preferably brought to substantially the same temperature as the non-aqueous phase before mixing the two phases. In this connection "substantially the same temperature" is intended to mean such temperature that after mixing the complete emulsion has a temperature at which the non-aqueous phase would have formed a homogeneous liquid. Low temperature processing may thus be possible for those non-ionic emulsifiers or emulsifier mixtures that are liquid at room temperature. Generally, the aqueous phase is added to the non-aqueous phase. In addition, although the shear rate used for mixing will affect to some extent the ultimate droplet size of the emulsion, the actual shear rate used is not critical in most cases for formation of the emulsion. Use of too high a shear rate with relatively viscous emulsions can result in destabilization of the emulsion system. The emulsions of the invention are suitably prepared under using mixers providing shear rates within the range of 1000–3000 rpm. Suitable information on shear rates and fluid behavior in mixing vessels can be found in Perry's Chemical Engineer's Handbook, sixth edition, D. Green (editor), McGraw-Hill, 1984. Thus, although both high and low shear rate mixers can be used, high shear rate mixers are generally preferred. The resulting microemulsion made in accordance with the invention is clear. This is shown by the phase diagrams, FIGS. 1 and 2. As shown thereon, using Cremophor RM 40 and RM 60 a curve established by certain points determines the phase boundary between the clear phase I and the cloudy phase II. Phase I is the microemulsion.

The rheological behavior of liquid dispersions provides information about the molecular structure of substances. It is important to maintain the structure of the dispersion. In this study, the strain sweep was used to predict the strength of the sample internal structure.

Figure 3:
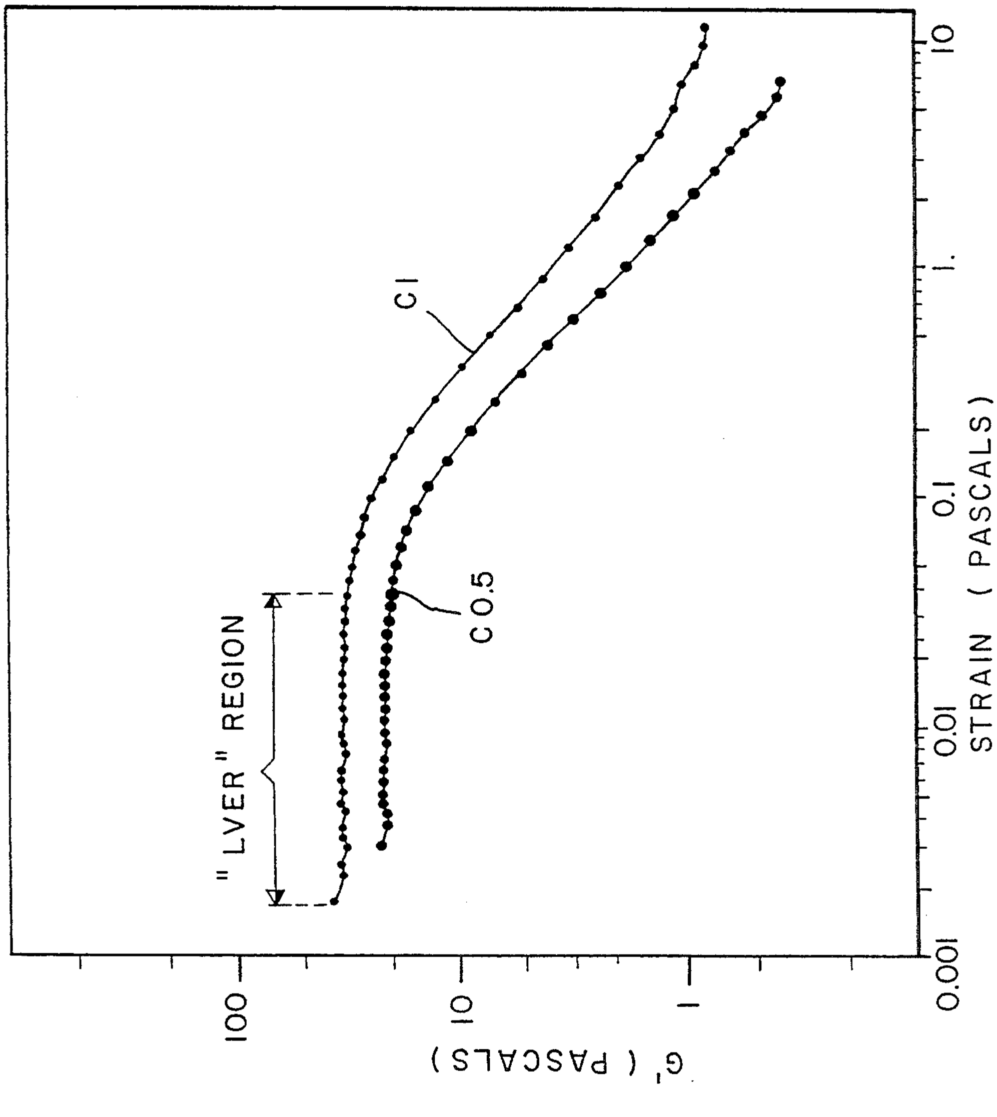
FIG. 3 is a graph showing a plot of G, modulus of elasticity, versus strain and is called a strain sweep.
Figure 5:
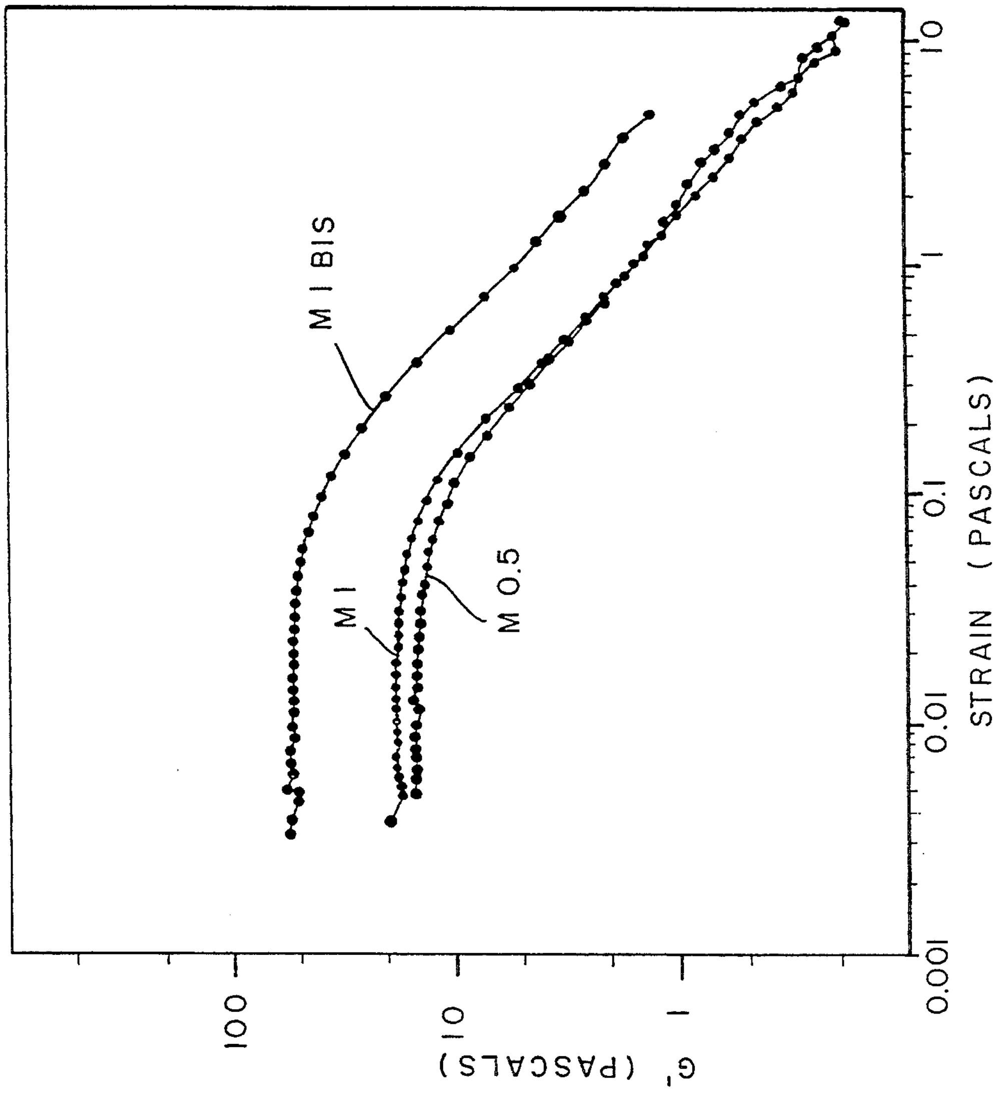
FIG. 5 is a graph showing a strain sweep with a different fabric softener base.

FIG. 3 showed the results of a strain sweep in order to determine the linear viscoelastic region LVER on the fabric softener. One should notice the logarithmic scale of the X and Y axis. The maximum strain a sample can sustain without showing non-linear behavior in the elastic modulus G′ can be used as a direct measurement of the strength of the sample's internal structure (G′ corresponds to the modulus of elasticity). This LVER region corresponds to the plateau region of the curves. FIG. 5 also shows the effect of the addition of 0.5% fragrance and 1% fragrance directly in the base HH00875/BC12232. An increase of fragrance concentration in the control increased the elastic modulus G′. But the size of the LVER region was not modified.

Figure 4:
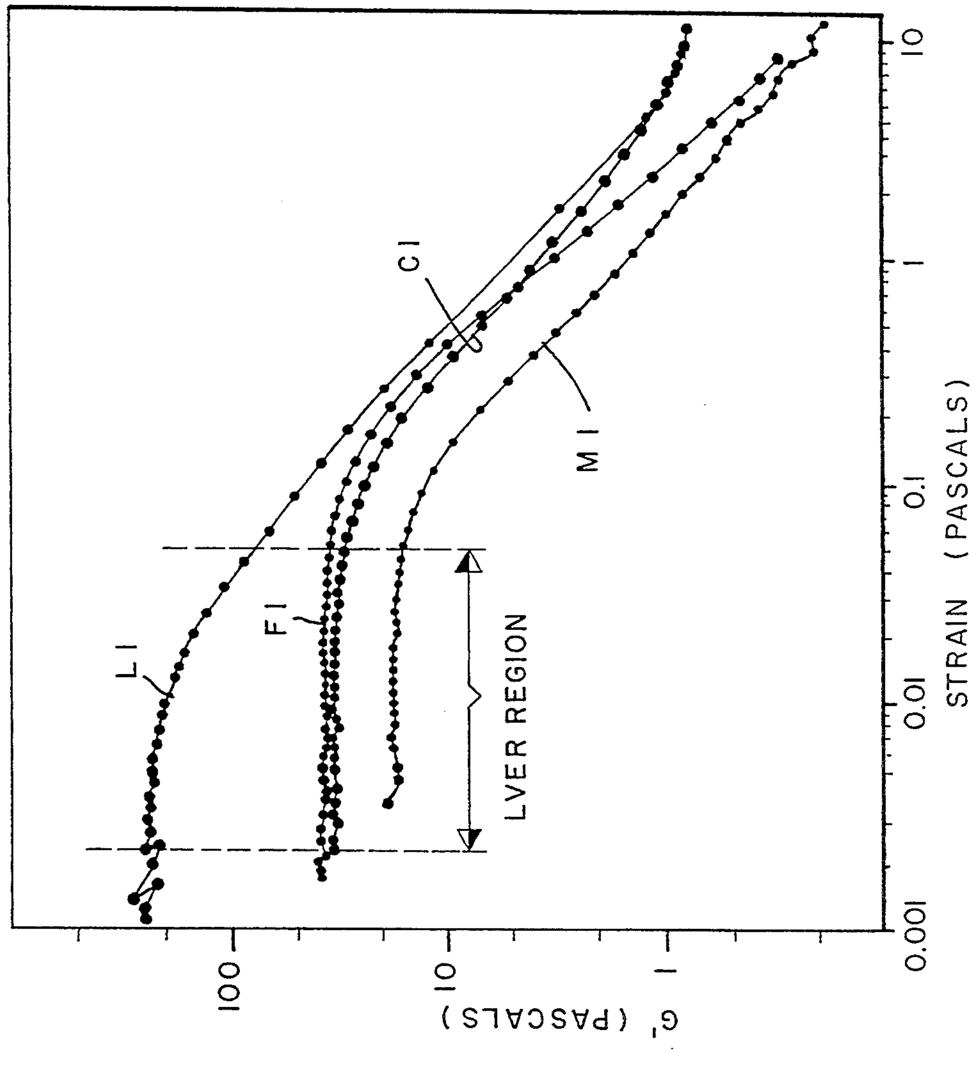
FIG. 4 is a graph showing a strain sweep of another system tested.

Different forms of the system were then investigated. A control was manufactured by adding the fragrance directly to the base (C1). FIG. 4 shows the reduction of G′, the elastic modulus, in the case of an introduction of microemulsified fragrance into the base (M1). Cremophor ® RH60 was used as the emulsifier. Addition of the fragrance in fragosomes (F1) to the base did not improve the results obtained with the control. On the other hand, the addition of the fragrance with a quaternary ammonium salt such as Luviquat ® (L1) resulted in a dramatic increase in viscosity. Therefore, it may be concluded that a microemulsion system can be used to reduce the viscosity of the system.

The nature of the base used in the preparation has a significant effect on the final viscosity. Indeed, microemulsions introduced in the initial base (labeled M1) and in the latest base labeled as M1 bis) exhibited large differences (FIG. 5). The nature of the base seemed to play an important role in the final result.

The symbol C 0.5 means that the control sample had a total fragrance concentration of 0.5% in the fabric conditioner base. The term M 0.5 means that it is a microemulsion sample with a fragrance concentration of 0.5% in the base.

The second kind of experiment performed involved the frequency sweep at 25° C. This type of experiment is important to determine the viscoelastic properties and is carried out in the linear viscoelastic region LVER in order to preserve the fragile structure. Oscillatory rheology within LVER probes the at rest structure of the viscometry. The dynamic frequency method gives access to several parameters:

(a) the elastic modulus G′, the viscous loss modulus G″ and the complex viscosity, n*, G′ is also called the storage modulus which represents a measure of the solid like behavior;

(b) the loss modulus G″ which is a measure of the liquid like behavior;

(c) the complex viscosity n* which is a characteristic of the flow behavior in the sample.

Figure 6:
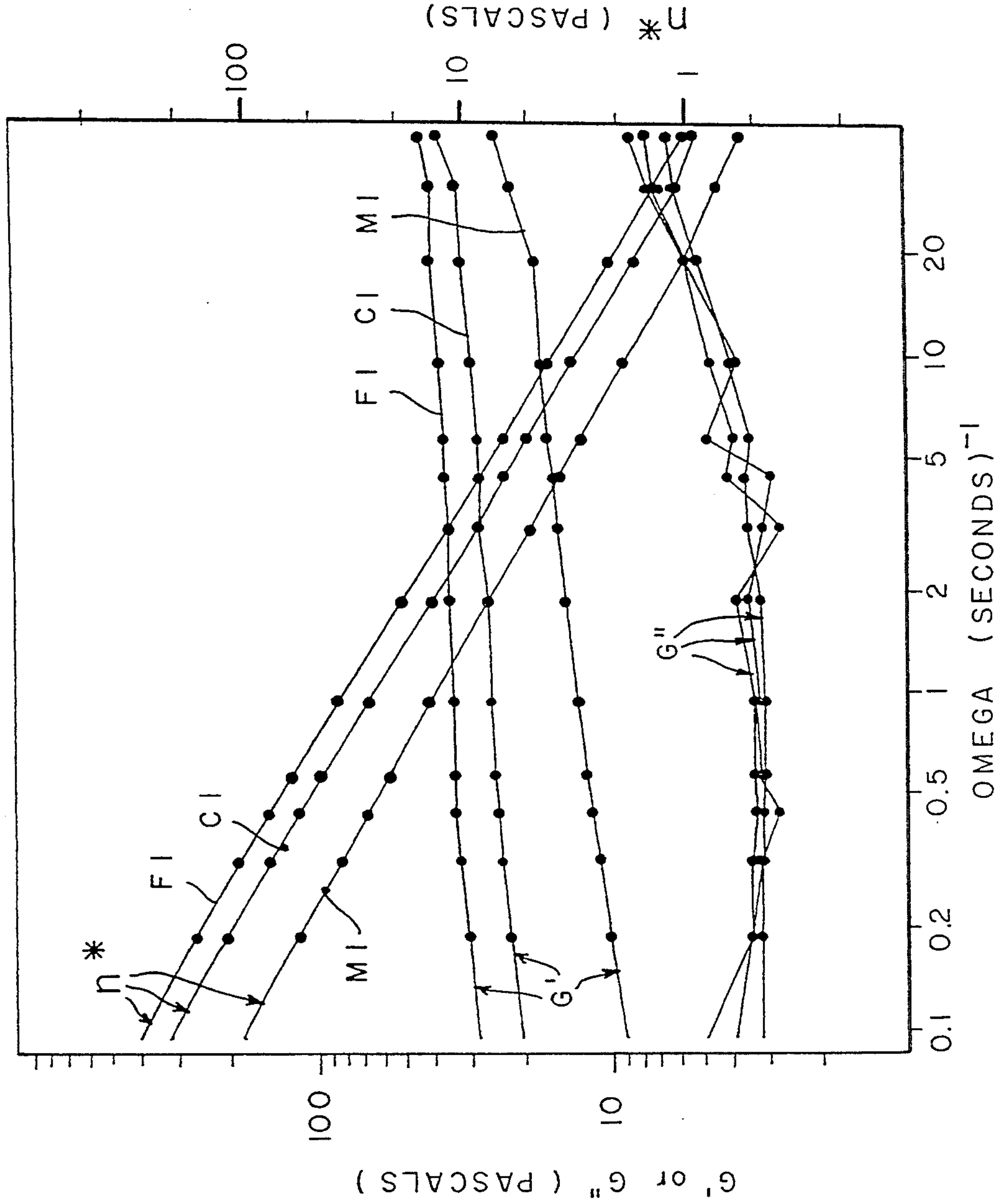
FIG. 6 is a graph representing the frequency sweeps.

The analysis of the frequency sweep (FIG. 6) confirmed the previous findings. It revealed a G′ larger than G″ which is characteristic of strongly associated particles. It showed that G″ is the same for all preparation studied. The differences in viscosity with microemulsified fragrance are the result of differences in G′. This decrease in viscosity is the result of a weakened structure. The addition of fragosomes reinforced the structure instead of weakened it.

Figure 7:
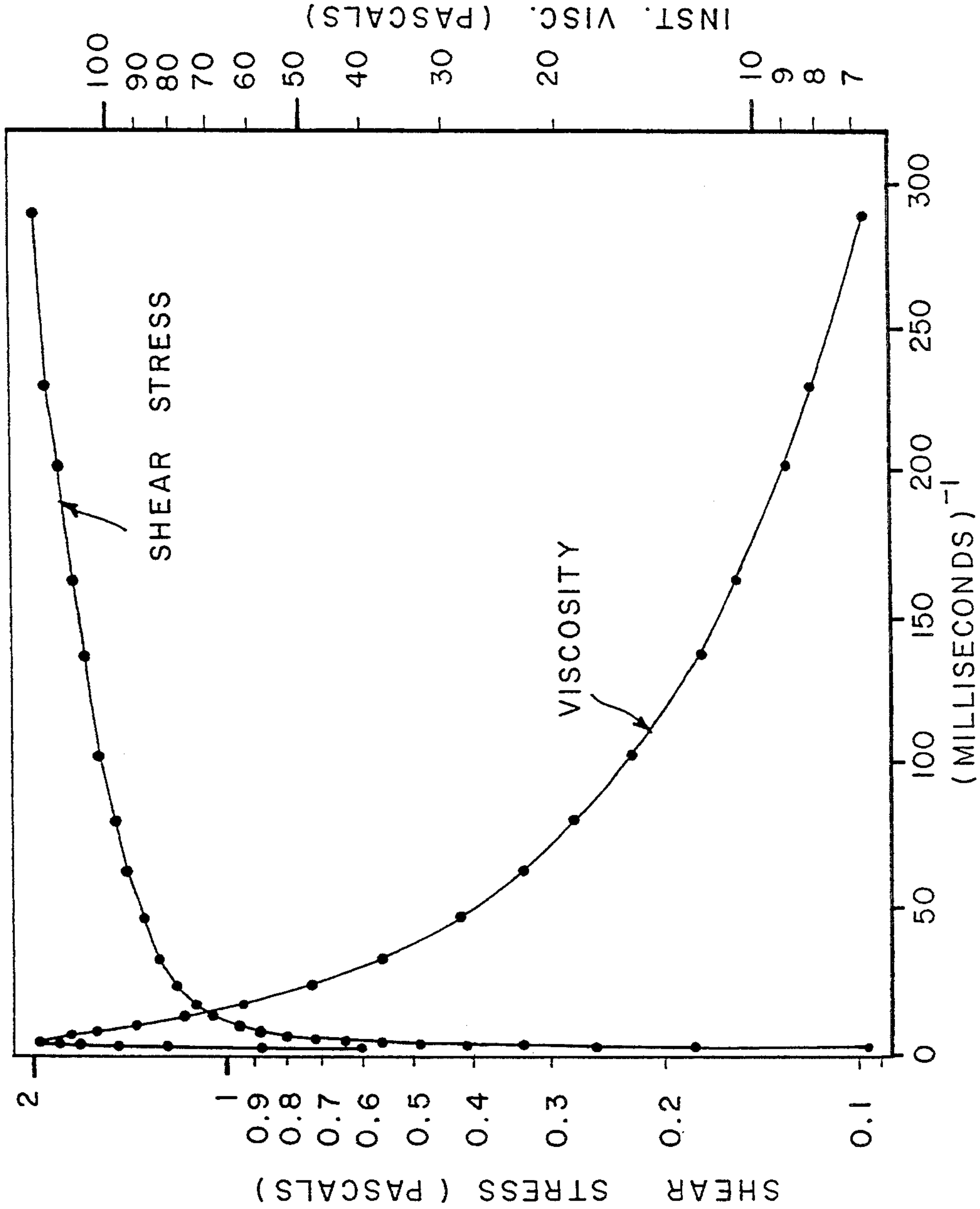
FIG. 7 is a plot of a yield stress test.

Finally a typical yield stress test (example in FIG. 7) allowed determination of the stress below which a material will not exhibit fluid like behavior over the time scale of practical interest. This resulted in a table of values:

| Sample | Yield Stress |
|---|---|
| Base I/0.5% Fragrance | 0.409 Pa |
| Base I/1% Fragrance | 0.643 Pa |
| Base I/Fragosome/1% Fragrance | 2.25 Pa |
| Base I/Microemulsion/0.5% Fragrance | 0.334 Pa |
| Base I/Microemulsion/1% Fragrance | 0.565 Pa |
| Base II/Microemulsion/1% Fragrance | 2.26 Pa |

The microemulsion system performed very well in base I, improving the viscosity compared to the control. But it should be noted that the change of base yielded dramatic differences. This is due to the fact that the unfragranced base II is also more viscous than base I.

A fundamental property of surfactants is their property of being adsorbed at interfaces. This property is micelle formation—the property that surface active agents have of forming colloidal size clusters in solution. Micelle formation is important because a number of important interfacial phenomena depend on the existence of micelles in solution. Evidence of the formation of micelles from the unassociated molecules of surfactant articles is a change in the conductivity of the solution. The sharp break in a curve of equivalent conductivity shows a sharp reduction in the conductivity of the solution. The concentration at which this phenomena occurs is called the critical micelle concentration or CMC. Similar breaks in almost every measurable physical property that depend on the size or number of particles and solution are shown by all types of surface active agents. The structure of micelle in aqueous media at concentrations not too far from the CMC and in the absence of additions that are solubilized by the micelle can be considered to be roughly spherical with an interior region containing the hydrophobic groups of the surface active molecules of radius approximately equal to the length of a fully extended hydrophobic group surrounded by an outer region containing the hydrated hydrophilic groups and bound water. Changes in temperature, concentration of surfactant additives in the liquid phase and structural groups in the surface active agent all may cause changes in the size, shape and aggregation number of the micelle. At least in some cases the surface active molecules are believed to form extended parallel sheets, 2 molecules thick with the individual molecules oriented perpendicular to the plane of the sheet. In aqueous solution, the hydrophilic heads of the surfactant molecules form the two parallel surfaces of the sheets and the hydrophobic tails comprise the inner region. In non-polar media, the hydrophobic groups of the surfactant molecules comprise the surfaces of the sheets; the hydrophilic groups comprise the interior. In both cases, solvent molecules occupy the region between parallel sheets of surfactants. In concentrated solution, surfactant micelles may also take the form of long cylinders packed together and surrounded by solvent. The lyophilic groups of the surfactant constitute the interior of the cylinders and the lyophobic groups comprise their interior. These ordered arrangements of extended micellar structures are called liquid crystalline phases.

For the usual type of polyoxyethylated non-ionic surfactant, the CMC in aqueous medium decreases with decrease in the number of oxyethylene units in the polyoxyethylene chain since this makes the surfactant more hydrophobic. Since commercial polyoxyethylated non-ionics are mixtures containing polyoxyethylene chains with different numbers of oxyethylene units cluster about some mean value, their CMC values are slighter lower than those of single species materials contained the same hydrophobic group.

For non-ionic polyoxyethylated alcohols and alkylphenols in aqueous media, empirical relationships have been found between the CMC and the number of oxyethylene units R in the molecule in the formula:

$$\log C_{cmc}=A'+B'R$$

wherein A' and B' are constants depending on the surface active agents. A table of representative contents is found in "Surfactants And Interfacial Phenomena" by Milton J. Rosen, published by John Wiley & Sons, 1978, page 103.

Some amounts of organic materials such as perfumes may produce marked changes in the CMC in aqueous media. A knowledge of the effects of organic materials on the CMC of surfactants is therefore of great importance both with theoretical and practical purposes.

Two types of materials markedly affecting the critical micelle concentrations in aqueous solutions of surfactants; namely, class 1 materials which are generally polar organic compounds and class 2 materials which are at concentrations usually much higher than the class 1 materials. Class 2 materials include urea, formamide, ethylene glycol and other polyhydric alcohols.

Choosing the correct surface active agent depends on many factors and is complicated by the fact that both phases, oil and water, are of favorable composition. The most frequently used method for selecting a suitable surface active agent is the HLB method (hydrophile-lipophile balance). In this method, on a scale to 0 to 40 it is possible to obtain an indication of the emulsification behavior of a surface active agent which is related to the balance between the hydrophilic and lipophilic portion of the molecule. A large number of commercial emulsifying agents have had an HLB number assigned to them. In some cases the HLB numbers and calculated from the structure of the molecule. The formula for some types of non-ionic surface active agents can be calculated from their structural groupings. Thus for fatty acid esters of many polyhydric alcohols the formula is:

$$HLB=20(1-S/A)$$

wherein S is the saponification number of the ester and A is the acid number of the fatty acid used in the ester. For esters where good saponification data is not readily obtainable, the following formula can be used:

$$HLB=E+P/5$$

wherein E is the weight percent of oxyethylene content and P is the weight percent of polyol content.

A commonly used general formula for non-ionics is:

$$HLB=20(M_h/M_h)+M_1$$

wherein $M_1$ is the formula weight of the hydrophilic portion of the molecule and $M_1$ is the formula weight of the lipophilic portion of the molecule. See Rosen, supra.

For purposes of the present invention, a surfactant with an HLB of 12 or greater is used.

The fragrance/surfactant compositions of the present invention contain a microemulsion of a fragrance component and a selected surface active agent as above wherein the fragrance component is dispersed and protected by the surface active agent.

The invention thus provides for the method for producing a protected stabilized emulsion of fragrance component and surface active agent and an improved fabric softener additive taken alone or further in conjunction with anti static agents and/or detergents and methods whereby various nuances can be imparted to the head space above the fabric treated with the fabric softener compositions, particularly with the wear of the fabric. These can be readily varied and controlled to produce the desired uniform character wherein one or more aromas have good initial strength and wherein one or more of the aromas is controllably released during use activity commencing with the wear of the fabric at a consisting high level over one or more extended periods of time.

Applicants have found that it is now possible to obtain a liquid fabric softener composition matter containing one or more fragrance compositions which provide fragrance release on use of extended high intensity and which permits control of viscosity so as to prevent gelation.

In the second embodiment of the invention the effect of encapsulation of a fragrance in a microemulsion on the substantivity properties was determined to be enhanced by use of a different class of surfactants. Thus, while control of viscosity is obtained by using microemulsion systems composed of high HLB surfactant which isolate the fragrance from the fabric softener droplets of vesicles, this system did not improve substantivity dramatically. A modification of the composition of the microemulsion system is believed to improve the substantivity profile. This is the reason why it was decided to include in the formulation some agents which would provide substantivity enhancement. The addition of a low HLB surfactants (Span®: Esters of sorbitol and fatty acids) in concentration 10 to 25% of the total surfactant concentration (0.8 to 2% of total fabric softener composition) to improve the final substantivity of the fragrance on wet clothes was carried out. This increased substantivity may be due to their adherence to clothes in the form of crystals structures and the affinity of the fragrance for this type of systems.

Figure 8:
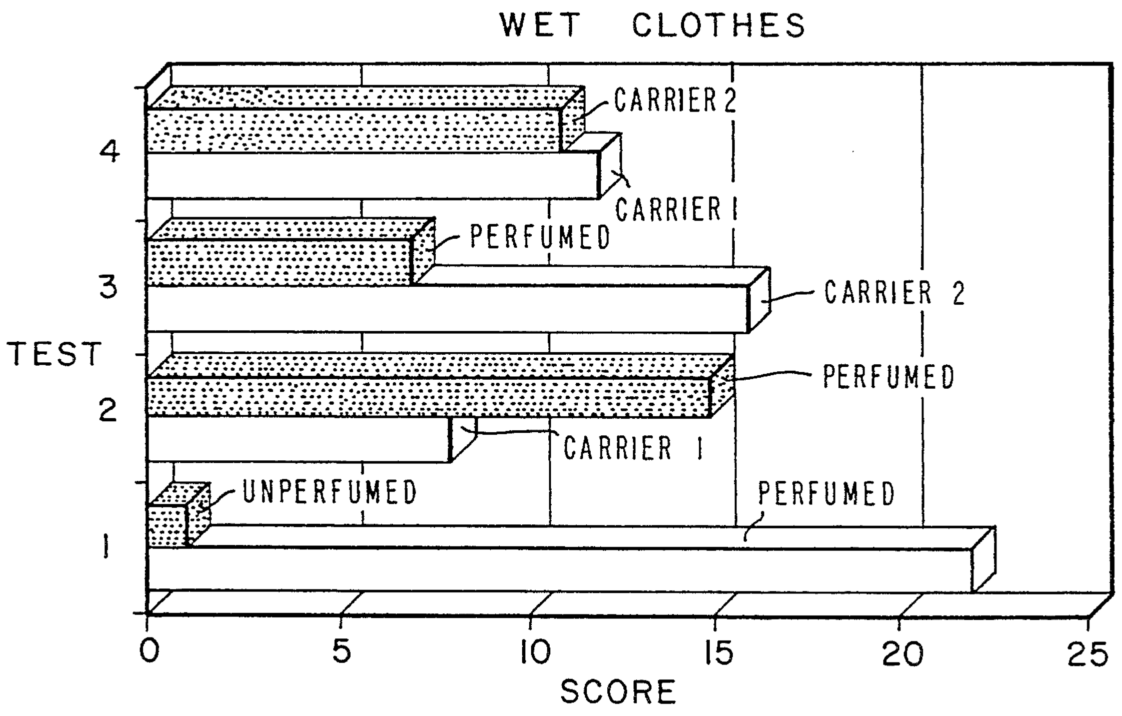
FIG. 8 and FIG. 9 are bar charts illustrating the substantivity effect obtained in accordance with the present invention.
Figure 9:
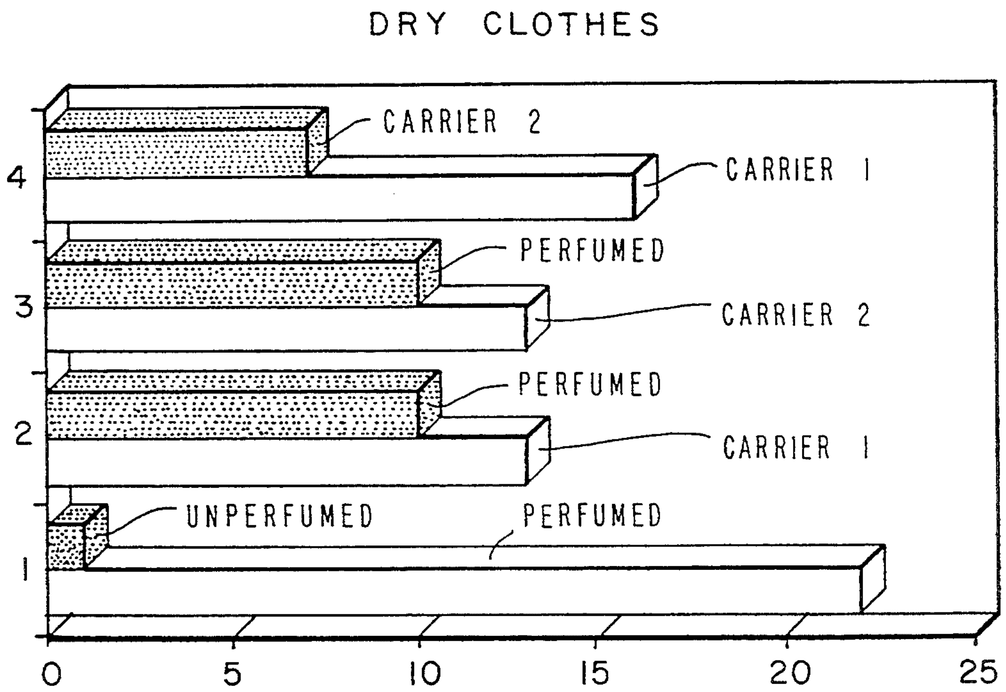

The graphs in FIGS. 8 and 9 report the effect of two types of carriers on the substantivity perceived by consumers. These systems were based on a high HLB surfactant with Span® 20. The results are superior and significant in the case of carrier 2 on wet clothes, and superior in the case of the two carrier tested on dry clothes, but the panel size did not allow us to establish a significance of the result. Low HLB surfactants as used herein means those that have a HLB of 10 or less.

Specific Embodiments

From about one part by weight up to about ten parts by weight of a non confined fragrance in alcoholic solution is dispersed in a surfactant of 90 to 99 parts by weight. By means of mechanical pressure the two materials are mixed together to form a stable emulsion.

Specific embodiment of the fabric softening agent, ten parts by weight of the fragrance emulsion concentrate described above are then mixed with a conventional fabric softening base formulation using a high shear mixture to produce a commercially suitable fabric softening formulation.

It is known that viscosity of a composition is a function of the concentration of the components and of temperature; i.e.

$$\eta = f(\eta_o T)$$

at a given temperature and concentration viscosity of the fabric softener composition can be expressed by the following relationship:

$$\eta_c = \alpha C_p^{+k1} + \beta C_s^{-k2} + \gamma C_{fs}^{+k3} + \delta (C_s C_p)^{-ky}$$

where $C_p$ is the perfume concentration $C_s$ is the surfactant concentration $C_{fs}$ is the concentration of the fabric softener base.

Constants $K_1$, $K_2$ etc. are dependent on the precise nature of the components. The coefficients $\alpha$, $\beta$, $\gamma$ etc. are specific for the components.

the change of viscosity $\Delta\eta$ can be expressed as:

$$\Delta\eta = \Sigma \int_{f1}^{f2} \left( \frac{\partial\eta}{\partial f} \right) \partial f$$

or $$\Delta\eta \int_{T_1}^{T_2} \left( \frac{\partial\eta}{\partial T} \right) \partial T + \int_{\eta_{c1}}^{\eta_{c2}} \left( \frac{\partial\eta}{\partial\eta_c} \right) \partial\eta_c.$$

The viscosity of a newly formulated composition is thus a function of the original viscosity, $\eta_o$ and the change in viscosity brought about by the change in concentrations of components, $$\eta = \eta_o + \Delta\eta.$$

We claim:

1. A method for controlling the viscosity of fabric softener compositions to thereby improve shelf life comprising:

forming a non-aqueous phase of a microemulsion of a perfume and a surfactant by mixing a perfume and a surfactant with an HLB number which is 12 or greater at a temperature where each of said perfume and surfactant is in the liquid state, and then mixing said non-aqueous phase under conditions of sufficient high shearing forces to uniformly disperse said perfume in said surfactant and to prevent air entrainment to thereby form a stable, clear microemulsion of said perfume in said surfactant, mixing together said clear microemulsion and a fabric softener base formulation in sufficient amounts to thereby form a fabric softener composition which avoids gelation.

2. The method according to claim 1 wherein the HLB number is 13 or greater.

3. The method according to claim 1 wherein 3 parts of the surfactant is used per part of perfume.

4. The method according to claim 1 further comprising mixing in a surfactant with a HLB number of 10 or less.

5. The method according to claim 1 wherein said surfactant is a non-ionic surfactant.

6. The method according to claim 5 which further comprises adding a cationic surfactant.

7. The method according to claim 1 which further comprises mixing said non-aqueous phase with an aqueous phase.

8. A method for improving the substantivity properties of fabric softener compositions comprising:

a first step of forming a microemulsion of a perfume and a surfactant by mixing a perfume and a surfactant with an HLB number which is 12 or greater at a temperature where each of said perfume and surfactant is in the liquid state, and under conditions of sufficient high shearing forces to uniformly disperse said perfume in said surfactant and to prevent air entrainment to thereby form a stable, clear microemulsion of said perfume in said surfactant, adding a surface active agent with a HLB number of 10 or less and mixing together said clear microemulsion, said surface active agent with a HLB of 10 or less and a fabric softener based formulation in sufficient amounts to thereby form a fabric softener compositions which avoids gelation and has improved substantivity.

* * * * *